US009427165B2

(12) United States Patent
Finlay et al.

(10) Patent No.: US 9,427,165 B2
(45) Date of Patent: Aug. 30, 2016

(54) HEURISTIC MANAGEMENT OF PHYSIOLOGICAL DATA

(71) Applicant: Corventis, Inc., St. Paul, MN (US)

(72) Inventors: Brion Finlay, Brooklyn Park, MN (US); Scott Williams, Minneapolis, MN (US); Richard Fogoros, Pittsburgh, PA (US); Brett Landrum, Shoreview, MN (US); Abhi Chavan, Osseo, MN (US)

(73) Assignee: Medtronic Monitoring, Inc., San Jose, CA (US)

(*) Notice: Subject to any disclaimer, the term of this patent is extended or adjusted under 35 U.S.C. 154(b) by 775 days.

(21) Appl. No.: 13/782,853

(22) Filed: Mar. 1, 2013

(65) Prior Publication Data

US 2013/0274584 A1    Oct. 17, 2013

Related U.S. Application Data

(60) Provisional application No. 61/606,188, filed on Mar. 2, 2012.

(51) Int. Cl.
| | |
|---|---|
| *A61B 5/04* | (2006.01) |
| *A61B 5/0432* | (2006.01) |
| *A61B 5/00* | (2006.01) |
| *A61B 5/08* | (2006.01) |
| *A61B 5/01* | (2006.01) |
| *A61B 5/0408* | (2006.01) |

(52) U.S. Cl.
CPC .......... *A61B 5/0432* (2013.01); *A61B 5/0006* (2013.01); *A61B 5/04012* (2013.01); *A61B 5/01* (2013.01); *A61B 5/04085* (2013.01); *A61B 5/04087* (2013.01); *A61B 5/0816* (2013.01); *A61B 5/4875* (2013.01)

(58) Field of Classification Search
CPC .. A61B 5/0006; A61B 5/01; A61B 5/04012; A61B 5/04085; A61B 5/04087; A61B 5/0432; A61B 5/0816; A61B 5/4875
See application file for complete search history.

(56) References Cited

U.S. PATENT DOCUMENTS

| | | | |
|---|---|---|---|
| 6,589,187 B1 * | 7/2003 | Dirnberger | A61B 5/0432 365/230.01 |
| 8,249,686 B2 | 8/2012 | Libbus et al. | |
| 8,374,688 B2 | 2/2013 | Libbus et al. | |
| 8,412,317 B2 | 4/2013 | Mazar | |
| 8,460,189 B2 | 6/2013 | Libbus et al. | |
| 8,578,118 B2 * | 11/2013 | Kleckner | A61B 5/0031 600/301 |
| 2009/0073991 A1 | 3/2009 | Landrum et al. | |
| 2009/0076336 A1 | 3/2009 | Mazar et al. | |

(Continued)

*Primary Examiner* — Amanda Patton
(74) *Attorney, Agent, or Firm* — Billion & Armitage; Michael A. Collins (57) ABSTRACT

Systems and methods for management of physiological data, for example data obtained from monitoring an electrocardiogram signal of a patient. In one example use, digital data is obtained and episodes of arrhythmias are detected. Snapshots of the digitized ECG signal may be stored for later physician review. One or more techniques may be used to avoid recording of redundant data, while ensuring that at least a minimum number of episodes of each detected arrhythmia can be stored. The system may automatically tailor its data collection to the cardiac characteristics of a particular patient. In one technique, memory is allocated to include for each detectable arrhythmia a memory segment designated to receive ECG snapshots representing only the respective arrhythmia. A shared memory pool may receive additional snapshots of as the designated memory segments fill.

19 Claims, 8 Drawing Sheets

(56) References Cited

U.S. PATENT DOCUMENTS

| | | |
|---|---|---|
| 2009/0076341 A1 | 3/2009 | James et al. |
| 2009/0076342 A1 | 3/2009 | Amurthur et al. |
| 2009/0076343 A1 | 3/2009 | James et al. |
| 2009/0076344 A1 | 3/2009 | Libbus et al. |
| 2009/0076345 A1 | 3/2009 | Manicka et al. |
| 2009/0076346 A1 | 3/2009 | James et al. |
| 2009/0076348 A1 | 3/2009 | Manicka et al. |
| 2009/0076349 A1 | 3/2009 | Libbus et al. |
| 2009/0076350 A1 | 3/2009 | Bly et al. |
| 2009/0076363 A1 | 3/2009 | Bly et al. |
| 2009/0076397 A1 | 3/2009 | Libbus et al. |
| 2009/0076401 A1 | 3/2009 | Mazar et al. |
| 2009/0076405 A1 | 3/2009 | Amurthur et al. |
| 2009/0076559 A1 | 3/2009 | Libbus et al. |
| 2009/0234410 A1 | 9/2009 | Libbus et al. |
| 2010/0234716 A1 | 9/2010 | Engel |
| 2011/0144470 A1 | 6/2011 | Mazar et al. |
| 2011/0245711 A1 | 10/2011 | Katra et al. |
| 2011/0270049 A1 | 11/2011 | Katra et al. |
| 2012/0101396 A1* | 4/2012 | Solosko .............. A61B 5/0006 600/509 |

\* cited by examiner

| RHYTHM TYPE | SIZE OF PRIVATE EPISODE RESERVE (EPISODES) | MAXIMUM RECORDING RATE (EPISODES/HR) | REFRACTORY PERIOD (MIN) | CROSS INHIBITION |
| --- | --- | --- | --- | --- |
| TACHYCARDIA 130-150 BPM | 20 | 2 | 10 | NO |
| TACHYCARDIA 150-165 BPM | 20 | 2 | 10 | NO |
| TACHYCARDIA 165-180 BPM | 20 | 2 | 10 | NO |
| TACHYCARDIA 180-250 BPM | 20 | 2 | 10 | NO |
| BRADYCARDIA | 20 | 2 | 10 | NO |
| PAUSE | 20 | 2 | 10 | NO |
| AFIB/FLUTTER ONSET | 20 | 2 | 10 | NO |
| AFIB/FLUTTER ONGOING | 20 | 2 | 30 | YES |
| AFIB/FLUTTER OFFSET | 0 | 0 | N/A | NO |
| MORPHOLOGY VT/VF | 20 | 2 | 10 | NO |
| AV BLOCK | 20 | 2 | 10 | NO |
| PATIENT TRIGGER | 20 | 2 | 10 | NO |
| PERIODIC ECG SNAPSHOT | 0 | 1 | 60 | YES |

HEURISTIC MANAGEMENT OF PHYSIOLOGICAL DATA

CROSS-REFERENCE TO RELATED APPLICATIONS

This application claims the benefit of U.S. Provisional Patent Application No. 61/606,188 filed Mar. 2, 2012 and titled "Heuristic Management of Physiological Data", the entire disclosure of which is hereby incorporated by reference herein.

BACKGROUND OF THE INVENTION

Electrocardiography is the interpretation of electrical activity in the heart, as measured by electrodes placed on the skin. Voltages measured between different electrodes undergo minute variations as a function of time, reflecting various stages of the operation of the heart. A recording or display of the voltages as a function of time is called an electrocardiogram, often abbreviated ECG or EKG.

To record a typical ECG, a number of electrodes are placed on a patient's skin, at least some of the electrodes on opposing sides of the patient's cardiac divide. As many as 10 or more electrodes may be used. Voltages measured between different pairs of electrodes are called "leads", and as many as 12 or more leads may be displayed or recorded in a complete ECG. However, meaningful analysis may be performed with only a handful of electrodes, even as few as two, in which case only one lead is available for recording.

Figure 1:
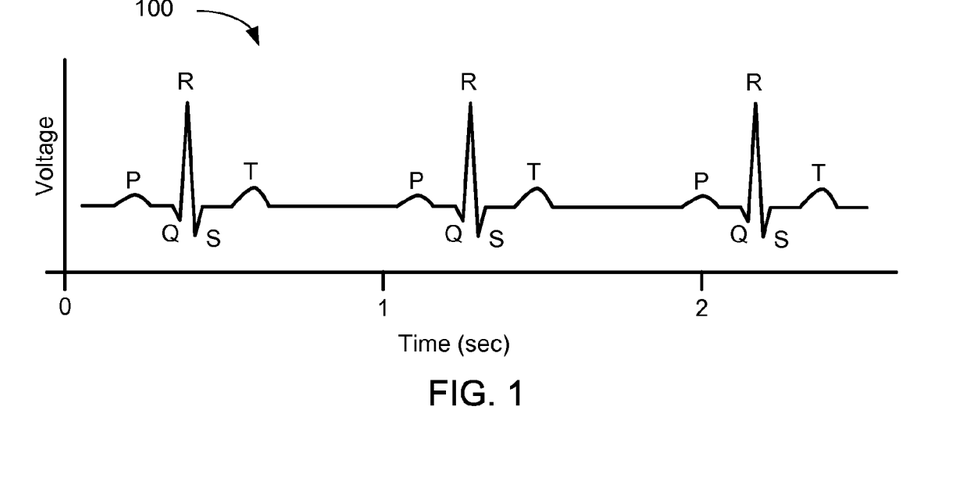
FIG. 1 illustrates a simplified single lead ECG.

An examination of the ECG can reveal valuable information about the functioning of the heart. For example, FIG. 1 illustrates a simplified single lead ECG 100 depicting a normal sinus rhythm, which is the normal beating of the heart. Each beat of the heart results in a complex of peaks and valleys, also called deflections, in the ECG, labeled P, Q, R, S, and T. The distance between the complexes reflects the time between heart beats, and therefore the heart rate, which is typically about 60-80 beats per minute for a resting patient, but depends somewhat on the patient's age, overall health, fitness level, and other factors.

Arrhythmias occur when the heart departs from the normal sinus rhythm, for example by beating unusually rapidly, unusually slowly, irregularly, or in an unsynchronized manner. Arrhythmias or other heart abnormalities may be diagnosed by examination of an ECG. For example, during atrial fibrillation, a common arrhythmia, the P deflections may be missing from the ECG. Many other specific ECG patterns have been identified and associated with particular arrhythmias.

Arrhythmias are often intermittent. For example, the heart may stay in a normal sinus rhythm for long periods between brief periods of arrhythmia. A single patient may also exhibit different kinds of arrhythmias at different times, or at the same time. If no filtering or data reduction were utilized, diagnosing intermittent arrhythmias would require recording a very long ECG and then laboriously scanning the ECG for periods of abnormality.

Automated ECG monitoring and identification of arrhythmias may be performed, and it is desirable that the results of such monitoring be presented in an efficient and complete manner.

BRIEF SUMMARY OF THE INVENTION

A system according to embodiments of the invention provides an intelligent, purposeful sampling of cardiac rhythms.

In one aspect, a method of collecting physiological data includes allocating in a memory a plurality of reserved blocks, each block designated for receiving data related to a respective one of a plurality of cardiac rhythm types. Digital data is obtained representing an electrocardiogram of a patient. From the digital data, an episode is detected of a particular one of the plurality of cardiac rhythm types in the patient. The method further includes storing, in the reserved block designated for receiving data related to the detected particular cardiac rhythm type, a data snapshot of the episode of the particular cardiac rhythm type. In some embodiments, the episode is a first episode, and the method further comprises assigning a respective refractory period to each of at least some of the plurality of rhythm types, detecting from the digital data a second episode of the particular cardiac rhythm type, and storing a data snapshot of the second episode of the particular cardiac rhythm type only if the respective refractory period of the particular cardiac rhythm type has elapsed since storing the data snapshot of the first episode. In some embodiments, the method further comprises assigning a respective maximum recording rate to each of at least some of the plurality of rhythm types, and storing a data snapshot of the second episode of the particular cardiac rhythm type only if doing so will not exceed the respective maximum recording rate of the particular cardiac rhythm type. In some embodiments, the particular cardiac rhythm type is a first rhythm type, and the method further comprises inhibiting the recording of further episodes of the first cardiac rhythm type based on the occurrence of an episode of a second cardiac rhythm type. In some embodiments, the episode is a first episode, and the method further comprises assigning a respective maximum recording rate to each of at least some of the plurality of rhythm types; detecting from the digital data a second episode of the particular cardiac rhythm type; and storing, in the reserved block designated for receiving data related to the particular cardiac rhythm type, a data snapshot of the second occurrence of the particular cardiac rhythm type only if doing so will not exceed the respective maximum recording rate of the particular cardiac rhythm type. In some embodiments, the particular cardiac rhythm type is a first rhythm type, and the method further comprises inhibiting the recording of further episodes of the first cardiac rhythm type based on the occurrence of an episode of a second cardiac rhythm type. In some embodiments, the episode is a first episode, and the method further comprises allocating in the memory a shared memory block; detecting from the digital data a second episode of the particular cardiac rhythm type; recognizing that the reserved block designated for receiving data related to the particular cardiac rhythm type has been filled; and storing, in the shared memory block, a data snapshot of the second episode of the particular cardiac rhythm type. The method may further comprise sensing a non-electrocardiogram physiological parameter of the patient, and adjusting at least one criterion for storage of electrocardiogram data snapshots based at least in part on the sensed non-electrocardiogram physiological parameter of the patient. The non-electrocardiogram physiological parameter of the patient may be selected from the group consisting of a bioimpedance of the patient, a hydration level of the patient, a respiration rate of the patient, an activity level of the patient, a posture of the patient, a temperature of the patient, and a reading from an accelerometer attached to the patient. Adjusting at least one criterion for storage of electrocardiogram data snapshots may include adjusting a refractory period assigned to one of the plurality of rhythm types. Adjusting at least one criterion for storage of electrocardiogram data snapshots may include adjusting a maximum recording rate assigned to one of the plurality of rhythm types. Adjusting at least one criterion for storage of ECG data snapshots may include inhibiting the recording of an electrocardiogram data snapshot. Adjusting at least one criterion for storage of electrocardiogram data snapshots may include triggering the recording of an electrocardiogram data snapshot.

In another aspect, a cardiac monitoring system comprises a processor and a memory. The memory comprises a data storage area and also stores instructions that are executable by the processor. The instructions configure the system to allocate in the memory a plurality of reserved blocks, each block designated for receiving data related to a respective one of a plurality of cardiac rhythm types; obtain digital data representing an electrocardiogram of a patient; detect from the digital data an episode of a particular one of the plurality of cardiac rhythm types in the patient; and store, in the reserved block designated for receiving data related to the detected particular cardiac rhythm type, a data snapshot of the episode of the particular cardiac rhythm type. In some embodiments, the cardiac monitoring system further comprises one or more sensors for sensing one or more non-electrocardiogram physiological parameters of the patient, and the instructions further configure the system to adjust at least one criterion for storing electrocardiogram data snapshots based at least on part on one or more of the sensed non-electrocardiogram physiological parameters. In some embodiments, the cardiac monitoring system further comprises an adherent device configured to be worn on the skin of the patient, and the adherent device includes electrodes for measuring the electrocardiogram of the patient. The processor and memory may be disposed in the adherent device.

In another aspect, a method of collecting physiological data comprises obtaining digital data representing an electrocardiogram of a patient, detecting from the digital data a first episode of one of the plurality of cardiac rhythm types in the patient, storing in an electronic memory a data snapshot of the first episode, and detecting from the digital data a second episode of one of the plurality of cardiac rhythm types in the patient. The method further comprises making one or more of the following determinations: whether a respective refractory period has elapsed since the most recent recording of a data snapshot of an episode of the same rhythm type as the second episode; whether storing a data snapshot of the second episode would exceed a respective maximum recording rate assigned to the rhythm type of the second episode; and whether recording of a data snapshot of the second episode is inhibited by the recording of a different data snapshot. The method further comprises evaluating whether storing of a data snapshot of the second episode is prohibited by the outcome of any one of the one or more determinations made, and storing in the electronic memory a data snapshot of the second episode only if such storing is not prohibited by the outcome of any of the one or more determinations made. In some embodiments, the method further comprises storing in the electronic memory an indication of the occurrence of each episode, regardless of whether a data snapshot of the episode is stored. In some embodiments, the method further comprises sensing a non-electrocardiogram physiological parameter of the patient, and adjusting at least one criterion for storage of electrocardiogram data snapshots based at least in part on the sensed non-electrocardiogram physiological parameter of the patient.

DETAILED DESCRIPTION OF THE INVENTION

Figure 2:
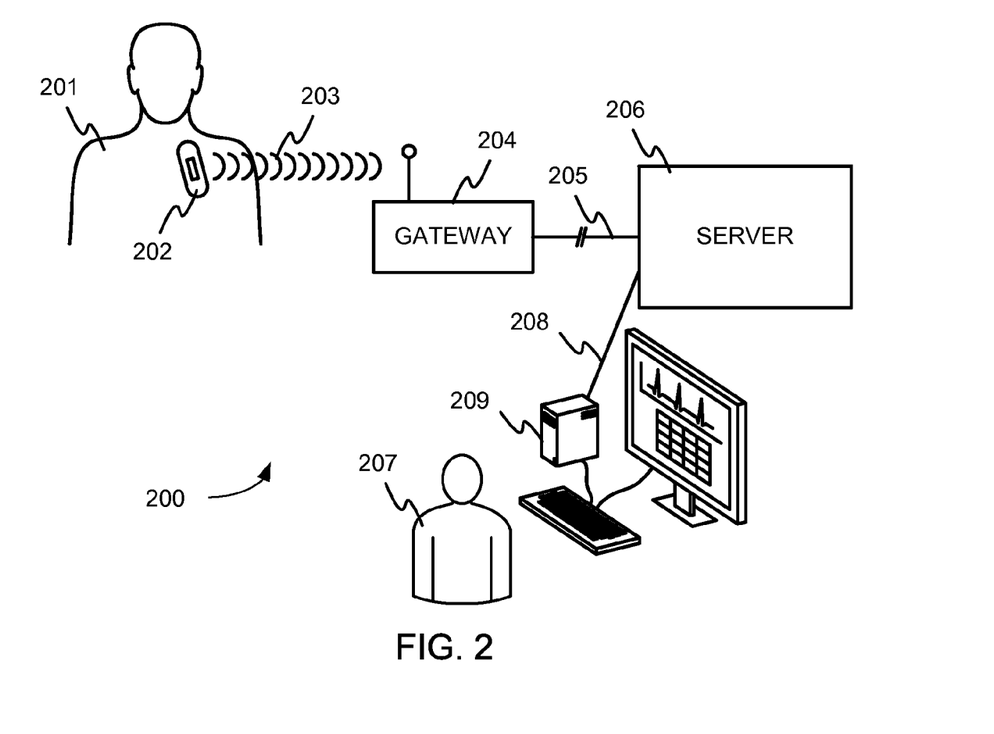
FIG. 2 illustrates an example system in which the invention may be embodied.

FIG. 2 illustrates an example system 200 in which the invention may be embodied. In example system 200, a patient 201 wears an adherent device 202 that includes electrodes in electrical contact with the patient's skin to receive electrical signals for reading an ECG. Adherent device 202 also includes electronics for monitoring, recording, and interpreting the electrical signals, and for transmitting data over a wireless link 203 to a gateway device 204. Gateway device 204 in turn relays data over a second data link 205 to a remote server 206, which may store the data for a large number of patients, and make the data available for review, for example by a clinician 207. In some embodiments, wireless link 203 may be bidirectional. Server 206 may present information in any suitable way, for example as pages served over a network 208 to a computer system 209 operated by clinician 207. Conveniently, computer system 209 may communicate with server 206 over the Internet, such that patient data can be reviewed at any location where Internet access is available.

While the invention may be embodied in systems having other configurations, system 200 is especially convenient for long term remote monitoring of patient 201. For example, adherent device 202 may stay in place on patient 201 for as much as a week or more, collecting data and transmitting information periodically to gateway 204, for forwarding to server 206. Adherent device 202 may include a battery, so that patient 201 is free to move so long as gateway 204 is within range of wireless link 203. Wireless link 203 may use any suitable wireless communication protocol, for example Bluetooth, IEEE 802.11, or another standardized protocol, or a proprietary protocol.

In many applications, server 206 resides at a centralized location, for example at a hospital, clinic, monitoring center, or other location far removed from patient 201. Gateway 204 receives data from adherent device 202 and forwards it to server 206 over a second communication link 205, which may be more suitable than wireless link 203 for long distance communication. For example, second communication link 205 may be wired or wireless telephone connection, so that information may be transferred from and to nearly any location worldwide. Conveniently, second communication link 205 may be a cellular telephone network and gateway 204 may include a cellular telephone transponder and a battery so that patient 201 can carry gateway 204, permitting monitoring to continue any place that cellular telephone service is available. When the patient is at home or otherwise in one location for an extended time, gateway 204 may be plugged into the power mains.

In addition to electrocardiography signals, adherent device 202 may be capable of measuring other signals and monitoring other non-electrocardiogram physiological patient parameters. For example, adherent device 202 may measure the patient's bioimpedance to evaluate the patient's hydration level or breathing, may include an accelerometer to measure the patient's posture or activity level, or may include a temperature sensor. Many other kinds of sensors and combinations of sensors are possible.

Figure 3A:
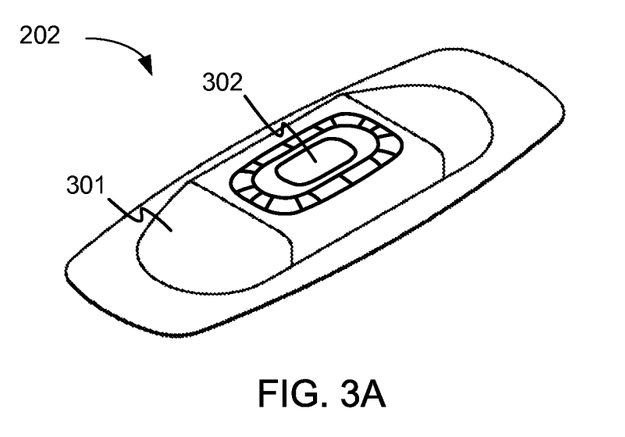
FIGS. 3A and 3B illustrate upper and lower perspective views of one example embodiment of adherent device.
Figure 3B:
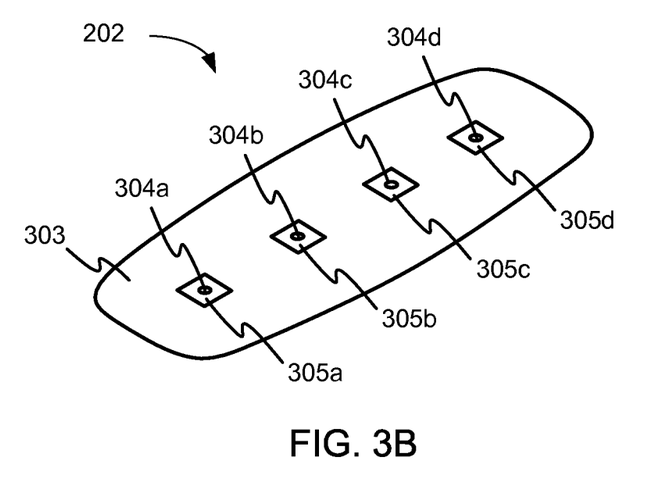

FIGS. 3A and 3B illustrate upper and lower perspective views of one example embodiment of adherent device 202. In the embodiment of FIGS. 3A and 3B, a soft cover 301 encloses the inner components of adherent device 202. A display 302 may be provided for indicating the status of adherent device 202. An adhesive layer 303 is configured to adhere to the patient's skin, keeping electrodes 304a-304d in contact with the patient's skin. Electrodes 304a-304d may be covered by gel patches 305a-305d to enhance electrical continuity between the skin and electrodes 304a-304d.

Figure 3C:
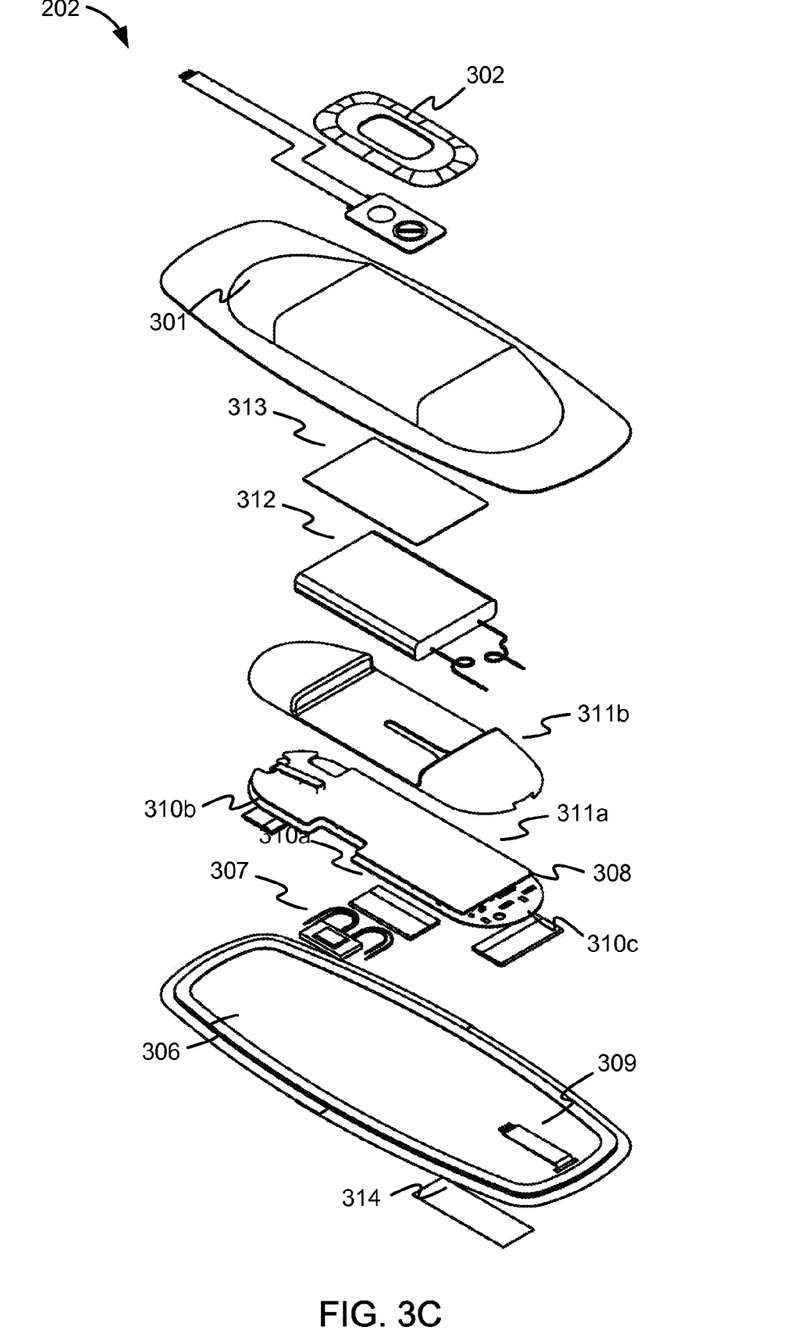
FIG. 3C illustrates an exploded view of the example adherent device of FIGS. 3A and 3B.

FIG. 3C illustrates an exploded view of example adherent device 202. A support 306 may include adhesive layer 303. A temperature or heat flux sensor 307 may be included. A printed circuit board 308 holds electronic components, and is connected to electrodes 304a-304d (not visible in FIG. 3C) via a flex circuit 309. Bridging loops 310a, 310b, and 310c (and a fourth bridging loop not visible) connect printed circuit board 308 to support 306. Circuit board covering components 311a and 311b may be provided for protecting printed circuit board 308 and supporting a battery 312, which may be covered by a battery cover 313. A label 314 may be provided at any convenient location on adherent device 202. Other arrangements of components are possible.

In one example embodiment, adherent device 202 may be or may be similar to a PiiX® adherent device manufactured by Corventis, Inc. of San Jose, Calif., USA, and gateway 204 may be a zLink® Mobile Transmitter also manufactured by Corventis Inc. Other examples of adherent devices, gateway devices, and other devices that may be used in embodiments of the invention may be found in the following U.S. patent applications, the entire disclosures of which are hereby incorporate by reference herein for all purposes: U.S. patent application Ser. No. 12/209,279 filed Sep. 12, 2008 and entitled "Multi-Sensor Patient Monitor to Detect Impending Cardiac Decompensation"; U.S. patent application Ser. No. 12/209,288 filed Sep. 12, 2008 and entitled "Adherent Device with Multiple Physiological Sensors"; U.S. patent application Ser. No. 12/209,430 filed Sep. 12, 2008 and entitled "Injectable Device for Physiological Monitoring"; U.S. patent application Ser. No. 12/209,479 filed Sep. 12, 2008 and entitled "Injectable Physiological Monitoring System"; U.S. patent application Ser. No. 12/209,262 filed Sep. 12, 2008 and entitled "Adherent Device for Cardiac Rhythm Management"; U.S. patent application Ser. No. 12/209,268 filed Sep. 12, 2008 and entitled "Adherent Device for Respiratory Monitoring"; U.S. patent application Ser. No. 12/209,269 filed Sep. 12, 2008 and entitled "Adherent Athletic Monitor"; U.S. patent application Ser. No. 12/209,259 filed Sep. 12, 2008 and "Adherent Emergency Patient Monitor"; U.S. patent application Ser. No. 12/426,497 filed Apr. 20, 2009 and entitled "Method and Apparatus to Measure Bioelectric Impedance of Patient Tissue"; U.S. patent application Ser. No. 12/209,273 filed Sep. 12, 2008 and entitled "Adherent Device with Multiple Physiological Sensors"; U.S. patent application Ser. No. 12/209,276 filed Sep. 12, 2008 and entitled "Medical Device Automatic Start-up upon Contact to Patient Tissue"; U.S. patent application Ser. No. 12/210,078 filed Sep. 12, 2008 and entitled "System and Methods for Wireless Body Fluid Monitoring"; U.S. patent application Ser. No. 12/209,265 filed Sep. 12, 2008 and entitled "Adherent Cardiac Monitor with Advanced Sensing Capabilities"; U.S. patent application Ser. No. 12/402,318 filed Mar. 11, 2009 and entitled "Heart Failure Decompensation Prediction Based on Cardiac Rhythm"; U.S. patent application Ser. No. 12/209,292 filed Sep. 12, 2008 and entitled "Adherent Device for Sleep Disordered Breathing"; U.S. patent application Ser. No. 12/721,821 filed Mar. 11, 2009 and entitled "Injectable Cardiac Monitor with Advanced Sensing Capabilities"; U.S. patent application Ser. No. 12/721,821 filed Mar. 11, 2009 and entitled "Injectable Cardiac Monitor with Advanced Sensing Capabilities"; U.S. patent application Ser. No. 12/209,278 filed Sep. 12, 2008 and entitled "Dynamic Pairing of Patients to Data Collection Gateways"; U.S. patent application Ser. No. 12/209,508 filed Sep. 12, 2008 and entitled "Adherent Multi-Sensor Device with Implantable Device Communications Capabilities"; U.S. patent application Ser. No. 12/209,528 filed Sep. 12, 2008 and entitled "Data Collection in a Multi-Sensor Patient Monitor"; U.S. patent application Ser. No. 12/209,271 filed Sep. 12, 2008 and entitled "Adherent Multi-Sensor Device with Empathic Monitoring"; U.S. patent application Ser. No. 12/209,274 filed Sep. 12, 2008 and entitled "Dynamic Pairing of Patients to Data Collection Gateways"; U.S. patent application Ser. No. 12/209,278 filed Sep. 12, 2008 and entitled "Dynamic Pairing of Patients to Data Collection Gateways"; U.S. patent application Ser. No. 12/209,294 filed Sep. 12, 2008 and entitled "Tracking and Security for Adherent Patient Monitor"; U.S. patent application Ser. No. 12/723,507 filed Mar. 12, 2010 and entitled "Method and Apparatus for Monitoring Fluid Content within Body Tissues"; U.S. patent application Ser. No. 12/958,910 filed Dec. 2, 2010 and entitled "Body Adherent Patch with Electronics for Physiological Monitoring"; U.S. patent application Ser. No. 12/910,076 filed Oct. 22, 2010 and entitled "Method and Apparatus for Remote Detection and Monitoring of Functional Chronotropic Incompetence"; and U.S. patent application Ser. No. 13/073,745 filed Mar. 28, 2011 and entitled "Method and Apparatus for Personalized Physiologic Parameters."

It will be recognized that the invention may be embodied in a wide variety of other system configurations. For example, in a hospital setting, electrodes may be connected directly by wires to monitoring equipment near the patient's bedside. In this situation, no adherent device or gateway device may be necessary. In some embodiments, adherent device 202 may transmit data directly to a remote server without using a gateway device. In other embodiments, adherent device 202 could transmit data directly to a computer system such as computer system 209, without utilizing a gateway or remote server. Many other variations are possible. While the discussion below assumes the configuration of system 200, the invention is not so limited.

Figure 4:
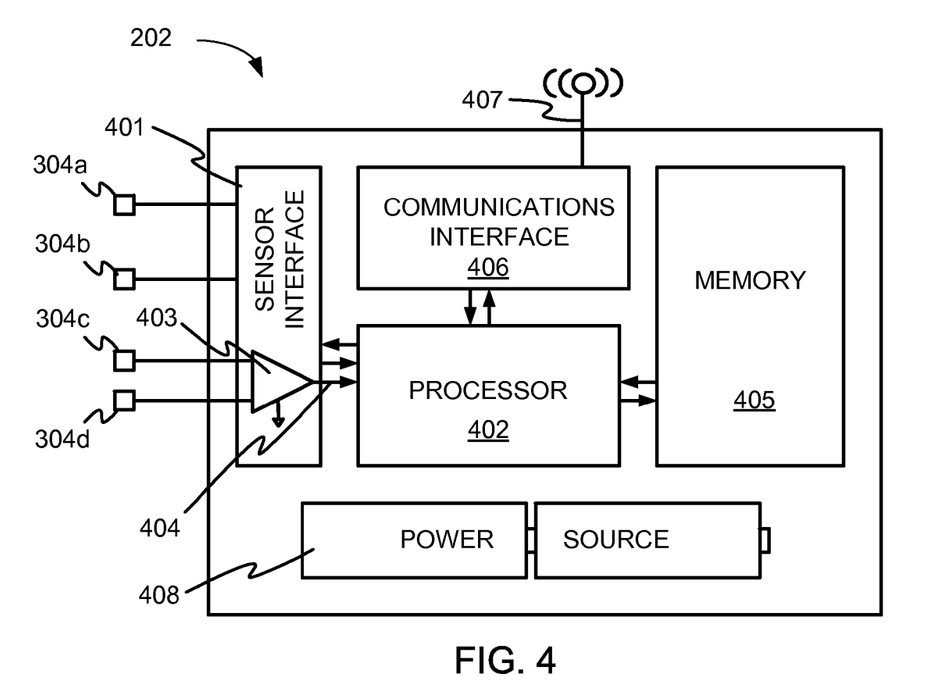
FIG. 4 illustrates simplified schematic diagram of an example electronic architecture of an adherent device.

FIG. 4 illustrates simplified schematic diagram of an example electronic architecture of adherent device 202. Electrodes 304a-304d may be integral with adherent device 202, and may be affixed to the patient's skin in selected locations such that at least two of the electrodes 304a-304d produce signals from which and ECG can be determined. Electrodes 304a-304d may be connected to sensor interface electronics 401, which may include signal conditioning circuitry such as amplifiers, filters, and the like, to condition signals from electrodes 304a-304d for presentation to a processor 402. In the embodiment of FIG. 2, an amplifier 403 produces a voltage signal 404 that represents the differential voltage present between electrodes 304c and 304d, although this may be a highly simplified and conceptual representation of the functioning of sensor interface electronics 401. Many other signals may pass between sensor interface electronics 401 and processor 402, and sensor interface electronics 401 may perform other functions as well, for example driving two of electrodes 304a-304d with a voltage to measure the impedance between two other electrodes, to characterize the patient's bioimpedance. At least some of electrodes 304a-304d may perform different functions at different times, with the functions controlled and selected by sensor interface electronics 401 under the control of processor 402. While the system of FIG. 4 results in a single-lead ECG measured from the patient's thorax, the invention is not so limited, and embodiments of the invention may be practiced with single- or multi-lead ECGs, and ECGs measured at other locations on the patient.

Processor 402 may be any suitable microprocessor, microcontroller, digital signal processor, or other similar device. Preferably, a signal representing the patient's ECG, for example voltage signal 404, is digitized so that processor 402 obtains a digitized ECG waveform. That is, processor 402 obtains a sequence of digital values that represent the magnitude of the ECG signal as a function of time. The digitization may be performed, for example, by an analog-to-digital converter (ADC) (not shown) residing at any convenient location within the system, for example within processor 402. Alternatively, an ADC may be provided at some other location in the system, for example as part of sensor interface electronics 401.

Adherent device 202 may further include a memory 405 accessible to processor 402. Memory 405 may be any suitable kind of memory, and may include for example random access memory (RAM), read only memory (ROM), programmable read only memory (PROM), erasable programmable read only memory (EPROM), electrically erasable programmable read only memory (EEPROM), flash memory, other kinds of memory, or combinations of memory types. Mass storage devices such as magnetic or optical disk storage devices may be used. Conveniently, memory 405 may include at least some flash memory, which is nonvolatile and readily written and re-written by processor 402. Memory 405 stores instructions that when executed by processor 402, enable processor 402 to control the operation of adherent device 202 and to perform computations in accordance with embodiments of the invention. Memory 405 also stores data relating to the patient's ECG, as is explained in more detail below.

Example adherent device 202 further includes communications interface circuitry 406, for example for communicating wirelessly via antenna 407 with gateway 204. A power source 408, for example one or more batteries may also be present, for powering adherent device 202. Connections between power source 408 and other parts of adherent device 202 are omitted from FIG. 3 for clarity.

Processor 402 may sample the ECG signal hundreds of times per second, and thus the amount of raw data generated by the system over hours or days of monitoring is considerable. Storing and transmitting this amount of data may be cumbersome and expensive, and even if all of the raw data were transmitted to server 206, much valuable physician time may be consumed in examining the data for episodes of arrhythmia. Much of the data may be redundant and relatively uninformative. For example many of the samples may simply indicate that the patient's heart was in a normal sinus rhythm.

In accordance with embodiments of the invention, processor 402 continuously or periodically examines the digitized ECG waveform, identifies heartbeats, and classifies the beats into rhythm types. Techniques for classifying heartbeats are known in the art, and may generally involve comparing ECG data to data templates representing different rhythm types. For example, a particular beat may be classified as normal sinus rhythm, or as exhibiting a pattern characteristic of a particular arrhythmia. The timing of beats is preferably also considered, so rate-based arrhythmias such as tachycardia and bradycardia can be identified. A particular beat may receive more than one classification. Based on the beat classifications, "episodes" of particular rhythm types are identified. For example, processor 402 may determine that an episode of a rhythm type has begun when a predetermined number of consecutive beats have exhibited that rhythm type, when a certain percentage of the most recent N beats have exhibited the rhythm type, or based on some other criteria. The beginning of an episode may be termed the "onset"

Similarly, the end of an episode may be called the "offset" of the episode. Processor 402 may apply criteria to identify the offset of an episode. For example, the offset of an episode may be identified when a preselected number of beats no longer exhibits the rhythm type in question, when a certain percentage of the most recent N beats do not exhibit the rhythm type, or based on some other criteria. An episode of a particular rhythm type is then the period between the onset and offset of the rhythm type.

Upon detection of an episode of an arrhythmia, processor 402 may record in memory an indication that the episode occurred. Processor 402 may also record in memory 405 a snapshot of the digitized ECG waveform so that a clinician can inspect at least some of the raw data that were determined to exhibit the particular rhythm type in question. Each snapshot may record, for example, a few seconds to a few minutes of raw data, or some other amount. Not all of the episode need be recorded.

However, for multiple reasons, it may not be desirable to record a snapshot of every arrhythmia episode. For example, episodes of a particular rhythm type occurring closely spaced in time may likely be redundant and provide little diagnostic value, but recording snapshots of them would consume limited memory resources and require the expense of transmitting the snapshot data to the server. In addition, the redundant data may increase the time required to review the data. On the other hand, it is desirable that every arrhythmia type identified during the monitoring period be recorded.

Embodiments of the invention manage the recording of ECG snapshots in an intelligent way to ensure that all rhythm types are recorded, while presenting the monitoring results in an efficient and thorough manner. Preferably, the large volume of physiological data is sampled in a heuristic manner, such that the sampling process does not mask or lose physiological information that could be useful to a physician for diagnosing a patient condition or prescribing a therapy. The sampling may be done on the basis of a customized quota system applicable to the rhythm types detectable in the patient, and that is created based on well-known and widely accepted expectations of the occurrence of various cardiac arrhythmias. The system may use a variety of techniques.

Figure 5:
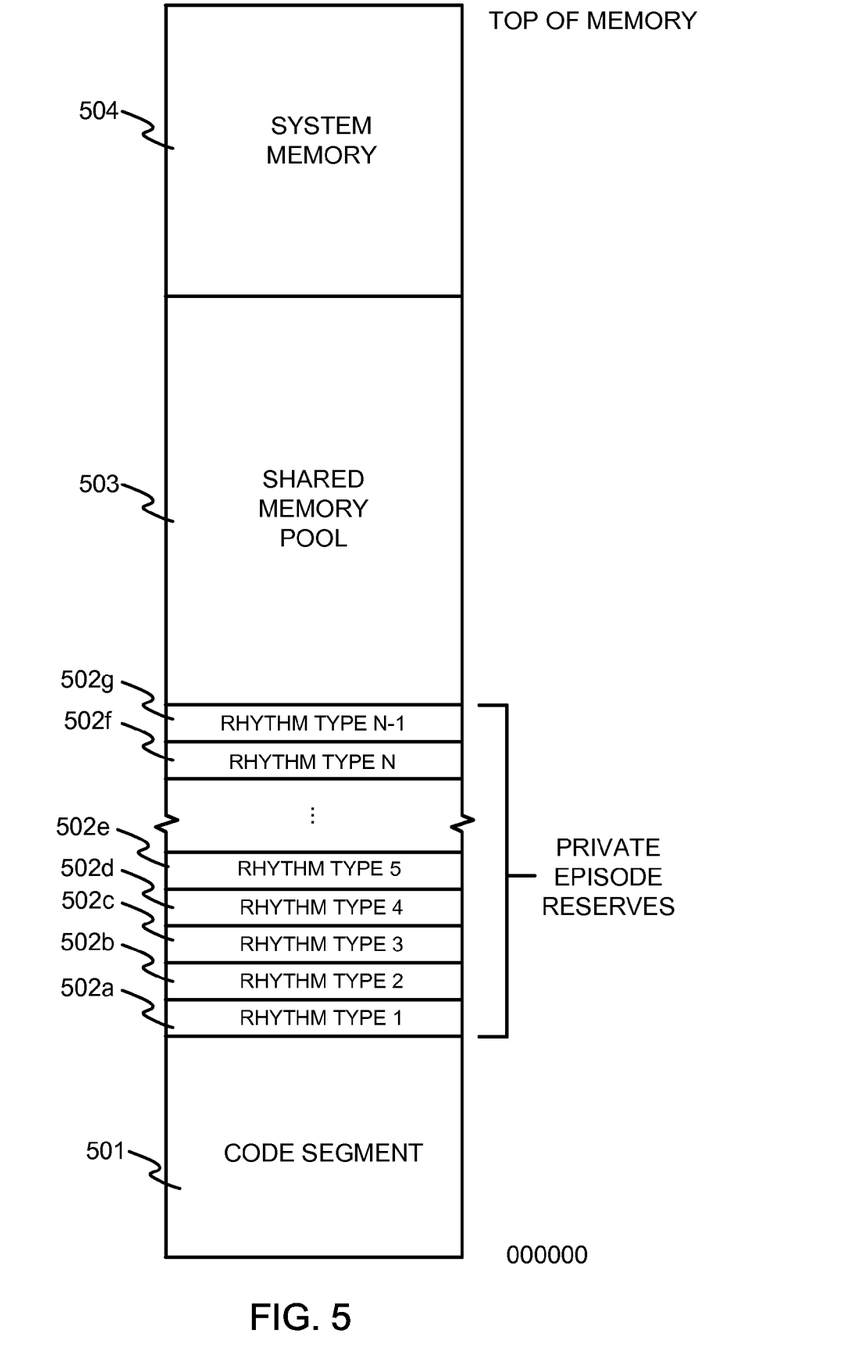
FIG. 5 illustrates a conceptual memory map according to embodiments of the invention.

In one aspect, memory 405 may be allocated into segments reserved for particular uses. In some embodiments, a private episode reserve is allocated for each detectable rhythm type. FIG. 5 illustrates a conceptual memory map of memory 405 according to embodiments of the invention. In the example of FIG. 5, a code segment 501 includes instructions for processor 402. Segments 501a-501g are private episode reserves, which are reserved blocks of memory designated for storing ECG snapshots of particular rhythm types. A shared memory pool 503 may store additional ECG snapshots when one or more private episode reserves are filled, as is described in more detail below. A system memory segment 504 may hold the processor stack, scratch space, program variable values, intermediate calculation results, and the like. It will be recognized that the organization of FIG. 5 is by way of example only, and other organizations may be used. No inference should be made that the sizes of the segments as shown in FIG. 5 is limiting. More or fewer segments may be present.

Each private episode reserve 502a-502g is sized to hold a specified number of snapshots of episodes of its respective rhythm type, and no snapshots of other rhythm types may ever be recorded in a private episode reserve. By way of example, private episode reserve 502d may be designated for recording of ECG snapshots exhibiting atrial fibrillation, and may be large enough to store 5, 10, 20, 50, or some other suitable number of ECG snapshots. When a first episode of atrial fibrillation is detected, an ECG snapshot may be taken and stored in private episode reserve 502d. Subsequent episodes of atrial fibrillation are handled similarly, until private episode reserve 502d is filled. After private episode reserve 502d is filled, any further ECG snapshots exhibiting atrial fibrillation would be stored in shared memory pool 503. The recording of ECG snapshots may be subject to other constraints as explained in more detail below.

Other detected rhythm types are handled similarly. For example, another one of private episode reserves 502a-502g may be reserved for recording ECG snapshots of episodes of tachycardia above 185 beats per minute. ECG snapshots exhibiting this particular arrhythmia would be stored in the designated private episode reserve until it is filled, and subsequent ECG snapshots would be stored in shared memory pool 503.

The number of private episode reserves will depend on the number of different rhythm types the system is configured to detect. The use of private episode reserves ensures that at least some number of ECG snapshots exhibiting each detected rhythm type can be stored. One frequently-occurring rhythm type cannot consume all of the system memory to the exclusion of recording ECG snapshots of other rhythm types. The size of the private episode reserves may be specified upon manufacture of the system, or may be configurable. For example when the system is applied to a particular patient, the sizes of the private episode reserves may be selected to reflect the expected behavior of the patient's heart. In some embodiments, the private episode reserves may be reconfigured during monitoring. For example, a clinician may use an Internet web site interface to transmit new parameters to adherent device 202 or gateway 204.

The recording of ECG snapshots may be subject to other limitations as well. For example, each recordable rhythm type may be assigned a maximum recording rate, such as 1, 2, or 4 snapshot recordings per hour, 1, 2, or 4 snapshot readings per day, or another suitable rate. The maximum recording rate limits the number of ECG snapshots that will be recorded for the respective rhythm type in a particular time period. For example, if the maximum recording rate for a particular rhythm type is two episodes per hour, ECG snapshots may be recorded (possibly subject to other rules) for the first two episodes of that rhythm type occurring within a particular hour, but no ECG snapshots will be recorded for any additional episodes occurring during the same hour. That is, ECG snapshots are recorded only when doing so will not exceed the maximum recording rate for the relevant rhythm type. The maximum recording rate limit ensures that the system will not consume all of its recording capability early in a monitoring period, and risk missing important rhythm episodes later in the recording period. The maximum recording rate reflects the assumption that similar episodes occurring close together in time are likely related to the same cause, and are likely to appear similar.

For an episode that would exceed the maximum recording rate and for which no ECG snapshot is recorded, the system may still optionally record in an event log an indication that the episode occurred. This indication may simply be an indication of the rhythm type that was detected and the onset and offset times of the episode, or a similar set of information. Such a record may consume only a few bytes of memory, as compared with the much larger size of an ECG snapshot.

In some embodiments, the recording of ECG snapshots may also be limited by assigning a refractory period to each respective rhythm type. The refractory period sets a minimum time that must elapse between recording ECG snapshots for a rhythm type. For example, a particular rhythm type may be assigned a refractory period of 10, 20, 30, or 60 minutes, or another suitable period. When refractory periods are used, an ECG snapshot will be recorded for a particular rhythm type only if at least the respective refractory period has elapsed since an ECG snapshot of that rhythm type was last recorded. In some embodiments, the refractory period may begin to run from the offset of an episode, and must elapse before the onset of the next episode in order for an ECG snapshot of the later episode to be recorded. The refractory period limitation also reflects the assumption that similar episodes occurring close together in time are likely related to the same cause, and are likely to appear similar, so that recording all of them would likely result in redundant data.

For an episode that occurs before the relevant refractory period has elapsed and for which no ECG snapshot is recorded, the system may still record in the event log an indication that the episode occurred.

In some embodiments, the recording of ECG snapshots may be limited by a process of cross-inhibition. That is, the recording of an ECG snapshot for a particular rhythm type may be suppressed by the recording of an ECG snapshot of another rhythm type, for example during the refractory period of the rhythm type to be inhibited. Cross-inhibition may be especially appropriate where the recording of the inhibited rhythm type waveform would be redundant, even though the recording of an ECG snapshot would otherwise be permitted by other rules such as a maximum recording rate or refractory period limitations. For example, episodes of atrial fibrillation may be ongoing over a period of days or more. The occurrence of this particular arrhythmia will initiate the recording of ECG snapshots regularly by the system, but any other ECG snapshot recorded for any other reason during such an extended period will also reflect the ongoing atrial fibrillation, so that recording an additional ECG snapshot specifically for the purpose of recording the atrial fibrillation would likely be redundant. The ECG snapshot recorded for the other purpose may still be flagged as indicating atrial fibrillation, as well as the rhythm type that caused it to be recorded, and an indication of the detection of atrial fibrillation may be recorded in the event log.

In another example of cross-inhibition, the system may be configured to periodically record an ECG snapshot even if no arrhythmias have been detected. For convenience, this periodic snapshot may be designated a "rhythm type", and assigned a maximum recording rate and a refractory period. The purpose of the periodic snapshot is to ensure that at least some minimum number of ECG snapshots is gathered during the monitoring period. However, if an ECG snapshot is recorded for any other reason during a particular interval, the purpose of the periodic snapshot is fulfilled by the ECG snapshot already recorded, and the periodic snapshot may be dispensed with. Any cross-inhibitions, including the inhibition of the periodic snapshot, are optional.

Figure 6:
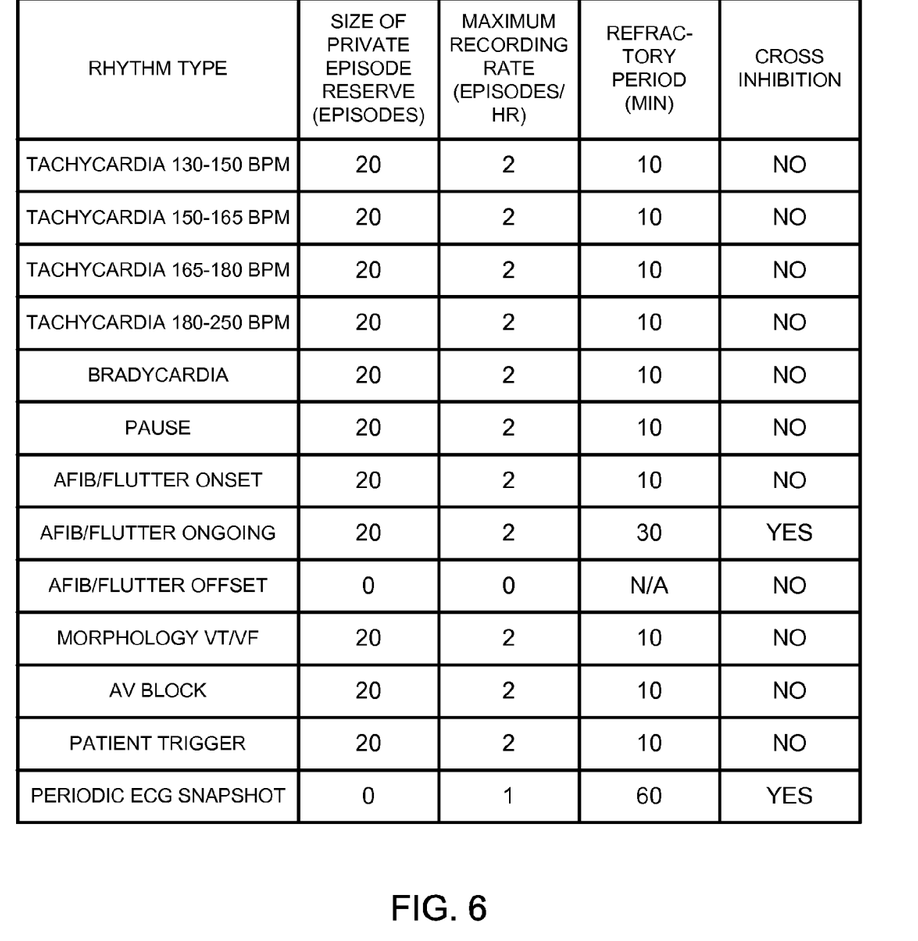
FIG. 6 is a table illustrating one example configuration of a system in accordance with embodiments.

FIG. 6 is a table illustrating one example configuration of a system in accordance with embodiments. In this example, 13 different rhythm types are identifiable by the system, and each is assigned certain parameters. For most rhythm types, private episode reserves are allocated, although this is not a requirement. In this example, the periodic ECG snapshot "rhythm type" is not allocated a private episode reserve, so that all periodic snapshots (if any) will be stored in the shared memory pool. Most of the rhythm types in the example configuration of FIG. 6 are assigned nonzero maximum recording rates, but this is also not a requirement. For example, the "Afib/Flutter Offset" type is assigned a maximum recording rate of zero, meaning that no ECG snapshots of this type will be recorded. Indications of the occurrences of episodes of this rhythm type may still be recorded in the event log. The table of FIG. 6 also indicates for which rhythm types ECG snapshot recording is inhibited by the recording of another rhythm type.

The "patient trigger" rhythm "type" is enabled by a switch, button, or other patient-actuatable device that allows the patient to arbitrarily trigger the recording of an ECG snapshot. For example, the patient may experience a symptom that he or she believes is heart related, and may signal the system to record an ECG snapshot at the time, in case the symptoms do not reflect an episode of a rhythm type that will be automatically detected by the system.

It will be understood that the particular parameters of FIG. 6, are by way of example only, and that different embodiments of the invention may utilize different numbers and kinds of rhythm types, sizes of the private episode reserves, assigned maximum recording rates, assigned refractory periods, and designations of cross-inhibition. Some embodiments may include some of these features and omit others. For example, an embodiment may use maximum recording rates, but not limit ECG recording by way of refractory periods. Other embodiments may limit ECG recording by way of refractory periods, but may not use maximum recording rates. Other embodiments may not use cross-inhibition. The sizes of the private episode reserves may be configured in any suitable way. It is to be understood that all workable combinations of features are considered to be disclosed.

A table such as the table of FIG. 6 may reside at any convenient location in the system, for example in memory 405 of adherent device 202, in gateway 204, or at server 206. The table may be hard coded, remaining fixed for the life of the system, or may be dynamically changeable. For example, after an initial portion of the monitoring period, it may be determined that too many or too few episodes of a particular rhythm type are being recorded, and parameters such as the maximum recording rate or refractory period of the rhythm type may be adjusted to alter the behavior of the system in ongoing monitoring.

Embodiments of the invention may provide for an intelligent sampling of cardiac episodes while ensuring that ECG snapshots can be recorded for any of several monitored rhythm types. The system may automatically adapt to the characteristics of a particular patient, as ECG snapshots of arrhythmias occurring more often can be stored in the shared memory pool after any private episode reserves are filled. The recording of at least some redundant data is avoided, and as a result, data storage and transmission costs can be constrained and valuable physician time required for reviewing the record is conserved.

While the selection of data for storage or eventual presentation may be done within adherent device 202, as described above, this is not a requirement. Embodiments of the invention may be implemented in other system components, for example gateway 204 or sever 206, if present, or in other system components or combinations of components. For example, adherent device may include minimal hardware that simply digitizes the ECG waveform and transmits the digital representation via wireless link 203 to gateway 204, which then performs the analysis required to identify particular rhythm types, and stores ECG snapshots and other information in a memory structure similar to that shown in FIG. 5 for later forwarding to server 206. Or adherent device 202 may recognize the rhythm types and transmit ECG snapshots to gateway 204, which may apply rules according to an embodiment of the invention to decide which snapshots to store and forward, and for which to simply indicate that episodes occurred without recording snapshots. Similarly, all raw data or snapshots of all rhythm type episodes could be transmitted to server 206, which could then identify rhythm type episodes, if necessary, and also apply rules according to an embodiment of the invention to decide what data to store. Other embodiments may not utilize a gateway or server. For example, adherent device 202 could transmit data directly to a self-contained bedside monitoring system, with the data reduction being performed within adherent device 202, within the bedside monitoring system, or by the combined efforts of adherent device 202 and the bedside monitoring system. Still other embodiments may not utilize an adherent device, but may collect data using conventional ECG electrodes connected by wires to a monitoring system. Many other configurations are possible.

Figure 7:
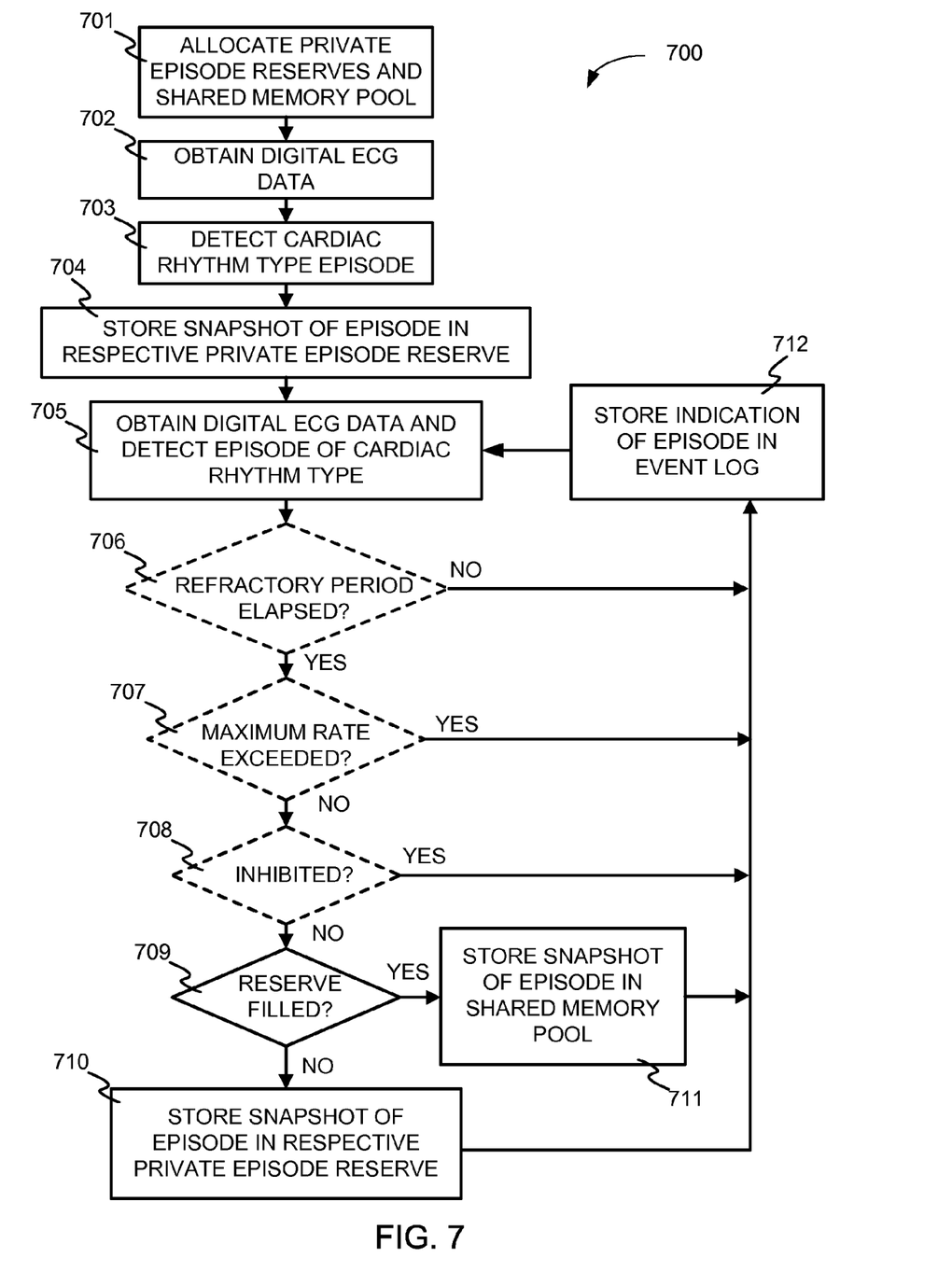
FIG. 7 illustrates a flowchart of a method according to embodiments of the invention.

FIG. 7 illustrates a flowchart of a method 700 according to embodiments of the invention. In step 701, memory is allocated to include a number of private episode reserves and a shared memory pool. In step 702, data representing a patient's ECG is obtained. In step 703, an episode of a cardiac rhythm type is detected. In step 704, an ECG snapshot of the detected episode is stored in the private episode reserve designated for the detected rhythm type. In step 705, another episode is detected, of the same or a different rhythm type.

Steps 706-708 are depicted in dashed lines, indicating that all of them, none of them, or any combination of them may be included in the method. In step 706, the time since the last recording of the most recently detected rhythm type is compared with the refractory period of that rhythm type. If the refractory period has not elapsed, no snapshot will be stored, and flow passes to step 712 where an indication of the occurrence of the episode is recorded. In step 707, the episode is checked to see if recording it would exceed the maximum recording rate for the particular rhythm type. If so, no snapshot will be stored, and flow passes to step 712. In step 708, it is determined whether recording of a snapshot for the detected episode is inhibited by the recording of another episode. If so, no snapshot will be stored, and flow passes to step 712.

In step 709, it is determined whether the private episode reserve corresponding to the detected rhythm type is full. If not, a snapshot of the episode is stored in the private episode reserve in step 710. If so, the snapshot is stored in the shared memory pool in step 711. In either case, once the snapshot is stored, flow passes again to step 712, and the system then continues to monitor the data for other rhythm type episodes. Thus, in the embodiment of FIG. 7, an indication of the occurrence of each arrhythmia episode is recorded in the event log regardless of whether an ECG snapshot of the episode is recorded. This technique may be used in other embodiments as well, and helps ensure that the fact that an arrhythmia episode occurred is documented, even if no snapshot is stored.

Figure 8:
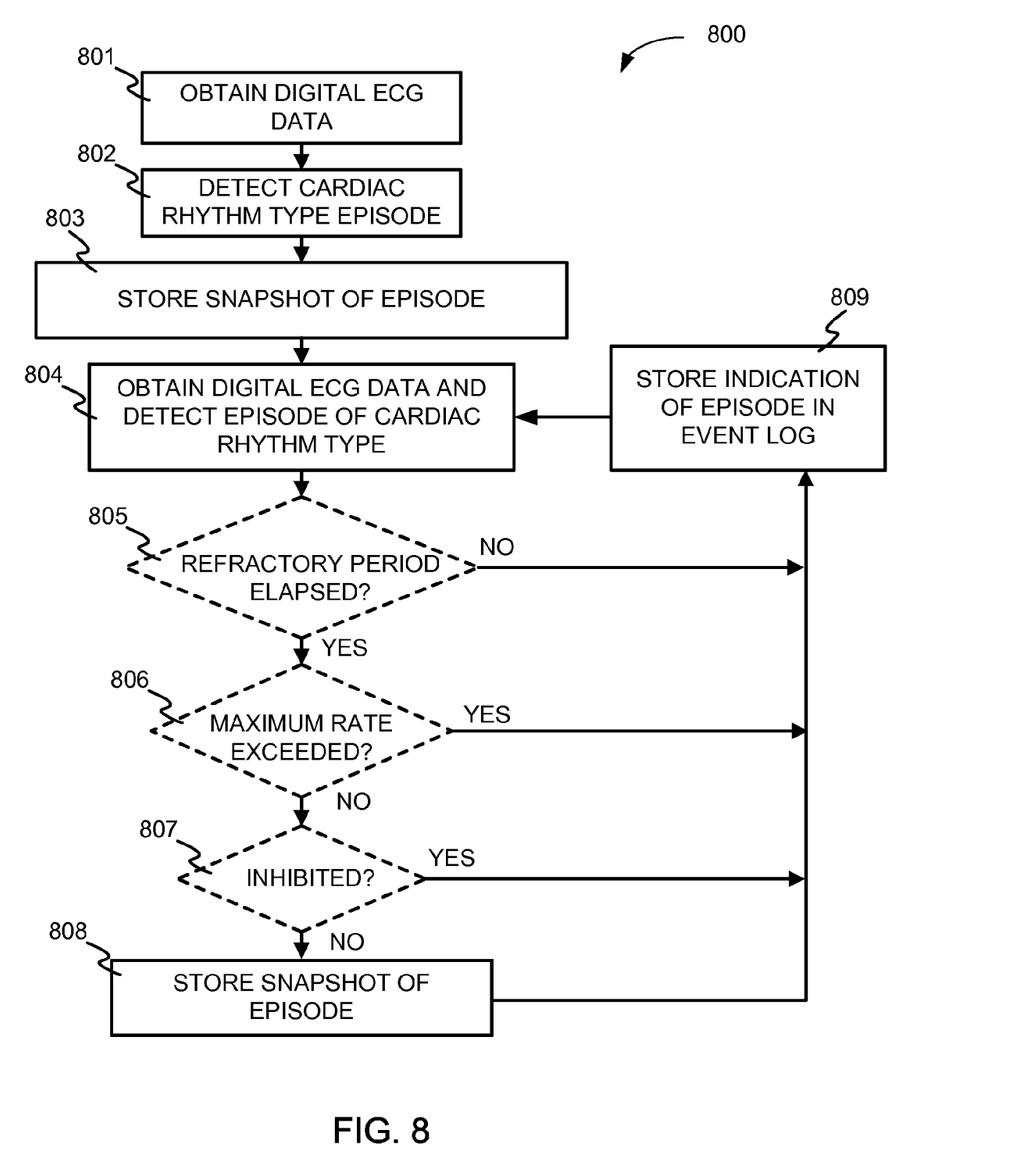
FIG. 8 shows a flowchart of a method according to another embodiment.

It will be recognized that method 700 is presented by way of example only, and other variations are possible. Embodiments may be envisioned where no private episode reserves are used, and all snapshots are stored in a large pool of shared memory. FIG. 8 shows a flowchart of a method 800 in accordance with this embodiment. In step 801, digital data representing a patient's ECG is obtained. In step 802, an episode of a cardiac rhythm type is detected. In step 803, an ECG snapshot of the detected episode is stored in memory. In step 804, another episode is detected, of the same or a different rhythm type.

Steps 805-807 are depicted in dashed lines, indicating that any one or any combination of them may be included in the method. In step 805, the time since the last recording of the most recently detected rhythm type is compared with the refractory period of that rhythm type. If the refractory period has not elapsed, no snapshot will be stored, and flow passes to step 809 where an indication of the occurrence of the episode is recorded. In step 806, the episode is checked to see if recording it would exceed the maximum recording rate for the particular rhythm type. If so, no snapshot will be stored, and flow passes to step 809. In step 807, it is determined whether recording of a snapshot for the detected episode is inhibited by the recording of another episode. If so, no snapshot will be stored, and flow passes to step 809. If snapshot recording is not prevented by any of the checks of steps 805-807, a snapshot of the detected episode is stored in step 808, an indication of the occurrence of the episode is stored in the event log at step 809, and control returns to step 804, where digital data is obtained and monitored for another episode detection.

As is described above, a system in accordance with embodiments of the invention may be able to sense physiological parameters of the patient other than ECG signals. These additional parameters may be termed "non-electrocardiogram" or "non-ECG" parameters, and may include such parameters as a bioimpedance reading of the patient, a patient activity level or posture, the patient's temperature, the patient's hydration level, the patient's respiration, or other parameters. In some embodiments, the system may adjust one or more criteria for storage of ECG data snapshots based at least in part on sensed non-ECG physiological parameter or parameters of the patient.

For example, adherent device 202 may include a capability for sensing a bioimpedance of the patient. In one example, embodiment, electrodes 304a-304d or other electrodes may be used to measure bioimpedance. Two of the electrodes, for example outer electrodes 304a and 304d, may be used to inject an alternating current through the patient tissue between the electrodes, and a voltage between inner electrodes 304b and 304c may be measured. The relationship of the injected current and the measured voltage is an indication of the impedance of the intervening patient tissue, also called a bioimpedance. Bioimpedance is affected by the patient's hydration level, and may also be affected by body movements such as chest expansion and contraction during breathing. Thus the bioimpedance measurement can indicate the patient's hydration level, respiration rate, breath volume, or other parameters. More information about the detection and use of bioimpedance and parameters related to bioimpedance can be found in the patent applications previously incorporated by reference, for example U.S. patent application Ser. No. 13/073,745.

When the same electrodes are used for ECG capture and the measurement of non-ECG patient physiological parameters, a switching scheme may be used so that electrodes can perform different functions at different times. Such a scheme is described in U.S. patent application Ser. No. 12/209,288 previously incorporated by reference.

In another example of sensing a non-ECG patient physiological parameter, an accelerometer may be attached to the patient, for example within adherent device 202. The output of the accelerometer may indicate the patient's posture or activity level. In other embodiments, the patient's temperature may be sensed for example using a skin temperature sensor within adherent device 202. It will be recognized that one or more non-ECG patient physiological parameters may be sensed, alone or in any combination. Parameters other than those given above as examples may also be used.

Preferably, signals representing the sensed non-ECG patient physiological parameters or parameters are sent to the processor that implements a scheme for deciding when to store ECG data snapshots. For example, sensors included in adherent device 202 may provide their outputs directly to processor 402. In other embodiments, sensor readings may be transmitted to gateway device 204, server 206, or another location.

In some embodiments, the system may adjust one or more criteria for storage of ECG data snapshots based at least in part on the sensed non-ECG physiological parameter or parameters of the patient. Adjusting one or more criteria may include one or more of triggering the recording of an ECG data snapshot, inhibiting the recording of an ECG data snapshot, adjusting the refractory period assigned to a cardiac rhythm type, or adjusting the maximum recording rate assigned to a cardiac rhythm type.

In one example, the system may normally be configured to record instances of tachycardia (rapid heart rate) with a certain refractory period and maximum recording rate. However, the system may adjust one or more of these criteria when bioimpedance data indicate a high respiration rate, suggesting that the patient is exercising. Recording of ECG snapshots identified as tachycardia may be adjusted during detected exercise, to avoid collection of redundant or possibly misleading information. For example, the tachycardia rhythm type may be assigned a lower maximum recording rate or a longer refractory period during periods of identified exercise, or recording of ECG data snapshots indicating tachycardia may be inhibited during identified exercise periods. As is described above, even when the recording of an ECG snapshot is inhibited, indications that episodes of the rhythm type may still be recorded in the event log.

Non-ECG physiological parameters may be used in combination, to further refine embodiments of the invention. For example, while a high respiration rate may suggest that the patient is exercising, there may be other explanations for the high respiration rate as well. In this situation, other parameters may be used to improve the confidence of the inference that the patient is exercising. For example, if the high respiration rate is accompanied by a large breath volume, the determination that the patient is exercising is reinforced. In another example, accelerometer data may be used to confirm that the patient is unusually active.

On the other hand, if a high respiration rate is accompanied by an unusually low breath volume, it may be suspected that the patient is not exercising, but is experiencing shortness of breath for another reason. Such a suspicion may be reinforced if accelerometer data indicates that the patient is at rest. In this case, rather than inhibit or slow the recording of ECG data snapshots, the recording of an ECG data snapshot may be triggered by the non-ECG physiological parameters. In other embodiments, the refractory period for a tachycardia rhythm type could be reduced, the maximum recording rate for a tachycardia rhythm type could be increased, or other adjustments may be made.

Many other uses of non-ECG physiological parameters may be envisioned for triggering, inhibiting, or adjusting the recording of ECG data snapshots. The use of non-ECG physiological patient parameters to inform the storage of ECG data snapshots may improve the reliability of the system, because the ECG data snapshots selected for recording have been vetted by use of the non-ECG parameters to help ensure that the limited number of ECG data snapshots actually recorded are physiologically relevant.

In some embodiments, the system may also detect when sensor failure occurs, for example, when electrodes of adherent device 202 have become disconnected from the patient's skin. This detach detection could be accomplished in any of a variety of ways, using different sensors or combinations of sensors. For example, detachment could be determined when a bioimpedance reading suddenly increases to a level that is not physiologically likely. In another example, a sudden decrease in the patient's apparent skin temperature may indicate that the temperature sensor (and therefore adherent device 202) is no longer properly attached to the patient's skin. In another example, accelerometer data may indicate a complete lack of activity for a period of time, suggesting that the adherent device is resting on a table, floor, or other surface rather than being attached to the patient. Many other detachment detection mechanisms may be envisioned.

The detection of sensor detachment may also be used in a manner similar to the non-ECG physiological parameters to inform the collection and storage or ECG data snapshots. For example, a suspected detachment detection may trigger the immediate recording of an ECG data snapshot, to verify that the ECG signal is also missing, confirming the detachment, or that the ECG signal is still present, indicating that the electrodes are not completely detached from the patient. In another example, storage of ECG data snapshots may be inhibited entirely upon the detection of sensor detachment, in order to avoid the costs of transmission and storage of data that is not reliable. Other uses of sensor detachment indications may be envisioned.

The table below gives examples of the use of non-ECG physiological parameter information and sensor detachment information to affect the collection and storage of ECG data snapshots. The examples are not intended to be limiting, and other embodiments may be envisioned within the scope of the appended claims, including embodiments in which different actions are taken than are shown in these examples for the same detected conditions.

| Non-ECG Physiological Parameter Sensed | Example Use of Non-ECG Parameter to Trigger Episode Capture and Storage | Example Use of Non-ECG Parameter to Inhibit Episode Capture and Storage | Example Use of Non-ECG Parameter to Change Refractory Period of a Rhythm Type | Example Use of Non-ECG Parameter to Change Maximum Recording Rate of a Rhythm Type |
|---|---|---|---|---|
| Hydration level | As hydration levels reach a specific set of conditions, may trigger collection of ECG to correlate. Examples: dehydration of active patients, decompensation | If the reading is above or below certain predetermined levels collection of data may be inhibited. | May collect on an ongoing basis after reaching trigger point | May collect on an ongoing basis after reaching trigger point |
| Respiration rate | When respiration rates reach a certain level, may trigger ECG capture. Example: looking for syncope related to symptoms of shortness of breath | When respiration rates reach a certain level, may inhibit recording of tachy events knowing that a patient is exercising | When respiration rates reach a certain level, may increase the refractory if need to look for more event separation | When respiration rates reach a certain level, may decrease the maximum rate limit to collect fewer tachy ECGs. |
| Accelerometer | (same as posture, activity level) | (same as posture, activity level) | (same as posture, activity level) | (same as posture, activity level) |
| Posture | May trigger on an at-rest posture to record episodes at night when the | May inhibit capture of certain episode types when patient is | | May increase the rate of ECG capture, for example |

-continued

| Non-ECG Physiological Parameter Sensed | Example Use of Non-ECG Parameter to Trigger Episode Capture and Storage | Example Use of Non-ECG Parameter to Inhibit Episode Capture and Storage | Example Use of Non-ECG Parameter to Change Refractory Period of a Rhythm Type | Example Use of Non-ECG Parameter to Change Maximum Recording Rate of a Rhythm Type |
|---|---|---|---|---|
| | patient is sleeping, especially looking for problems related to sleep disorders | standing | | increasing the rate of the "periodic ECG type" |
| Activity level | Same as respiration rate | Same as respiration rate | Same as respiration rate | Same as respiration rate |
| Detach Detection | May trigger collection of ECG to verify ECG signal | May inhibit collection of other ECGs to manage transmission costs | May collect ECGs on an ongoing periodic basis to continue to verify the ECG signal | May collect ECGs on an ongoing periodic basis to continue to verify the ECG signal |

While embodiments of the invention have been described in conjunction with real-time patient monitoring, the invention is not so limited. For example, techniques embodying the invention may be used to manage data storage requirements, such as to decide which episode snapshots are stored in online storage, and which are moved to offline storage.

The invention has now been described in detail for the purposes of clarity and understanding. However, those skilled in the art will appreciate that certain changes and modifications may be practiced within the scope of the appended claims.

What is claimed is:

1. A method of collecting physiological data, the method comprising:
    allocating in a memory a plurality of reserved blocks, each block designated for receiving data related to a respective one of a plurality of cardiac rhythm types;
    obtaining digital data representing an electrocardiogram of a patient;
    detecting from the digital data a first episode of a particular one of the plurality of cardiac rhythm types in the patient, wherein the particular cardiac rhythm type is a first cardiac rhythm type;
    storing, in the reserved block designated for receiving data related to the detected particular cardiac rhythm type, a data snapshot of the episode of the particular cardiac rhythm type; and
    inhibiting the recording of further episodes of the first cardiac rhythm type based on the occurrence of an episode of a second cardiac rhythm type.

2. The method of claim 1, wherein the episode is a first episode, the method further comprising:
    assigning a respective refractory period to each of at least some of the plurality of rhythm types;
    detecting from the digital data a second episode of the particular cardiac rhythm type; and
    storing a data snapshot of the second episode of the particular cardiac rhythm type only if the respective refractory period of the particular cardiac rhythm type has elapsed since storing the data snapshot of the first episode.

3. The method of claim 2, further comprising:
    assigning a respective maximum recording rate to each of at least some of the plurality of rhythm types; and
    storing a data snapshot of the second episode of the particular cardiac rhythm type only if doing so will not exceed the respective maximum recording rate of the particular cardiac rhythm type.

4. The method of claim 2, wherein the particular cardiac rhythm type is a first rhythm type, the method further comprising:
    inhibiting the recording of further episodes of the first cardiac rhythm type based on the occurrence of an episode of a second cardiac rhythm type.

5. The method of claim 1, wherein the episode is a first episode, the method further comprising:
    assigning a respective maximum recording rate to each of at least some of the plurality of rhythm types; and
    detecting from the digital data a second episode of the particular cardiac rhythm type; and
    storing, in the reserved block designated for receiving data related to the particular cardiac rhythm type, a data snapshot of the second occurrence of the particular cardiac rhythm type only if doing so will not exceed the respective maximum recording rate of the particular cardiac rhythm type.

6. The method of claim 1, wherein the episode is a first episode, the method further comprising:
    allocating in the memory a shared memory block;
    detecting from the digital data a second episode of the particular cardiac rhythm type;
    recognizing that the reserved block designated for receiving data related to the particular cardiac rhythm type has been filled; and
    storing, in the shared memory block, a data snapshot of the second episode of the particular cardiac rhythm type.

7. The method of claim 1, further comprising:
    sensing a non-electrocardiogram physiological parameter of the patient; and
    adjusting at least one criterion for storage of electrocardiogram data snapshots based at least in part on the sensed non-electrocardiogram physiological parameter of the patient.

8. The method of claim 7, wherein the non-electrocardiogram physiological parameter of the patient is selected from the group consisting of a bioimpedance of the patient, a hydration level of the patient, a respiration rate of the patient, an activity level of the patient, a posture of the patient, a temperature of the patient, and a reading from an accelerometer attached to the patient.

9. The method of claim 7, wherein adjusting at least one criterion for storage of electrocardiogram data snapshots comprises adjusting a refractory period assigned to one of the plurality of rhythm types.

10. The method of claim 7, wherein adjusting at least one criterion for storage of electrocardiogram data snapshots comprises adjusting a maximum recording rate assigned to one of the plurality of rhythm types.

11. The method of claim 7, wherein adjusting at least one criterion for storage of ECG data snapshots comprises inhibiting the recording of an electrocardiogram data snapshot.

12. The method of claim 7, wherein adjusting at least one criterion for storage of electrocardiogram data snapshots comprises triggering the recording of an electrocardiogram data snapshot.

13. A cardiac monitoring system, comprising:
a processor; and a memory, the memory comprising a data storage area and also storing instructions that are executable by the processor and configure the system to;
allocate in the memory a plurality of reserved blocks, each block designated for receiving data related to a respective one of a plurality of cardiac rhythm types;
obtain digital data representing an electrocardiogram of a patient;
detect from the digital data a first episode of a particular one of the plurality of cardiac rhythm types in the patient, wherein the particular cardiac rhythm type is a first cardiac rhythm type; and
store, in the reserved block designated for receiving data related to the detected particular cardiac rhythm type, a data snapshot of the episode of the particular cardiac rhythm type, wherein the recording of further episodes of the first cardiac rhythm type are inhibited based on the occurrence of an episode of a second cardiac rhythm type.

14. The cardiac monitoring system of claim 13, further comprising one or more sensors for sensing one or more non-electrocardiogram physiological parameters of the patient, wherein the instructions further configure the system to adjust at least one criterion for storing electrocardiogram data snapshots based at least on part on one or more of the sensed non-electrocardiogram physiological parameters.

15. The cardiac monitoring system of claim 13, further comprising an adherent device configured to be worn on the skin of the patient, wherein the adherent device includes electrodes for measuring the electrocardiogram of the patient.

16. The cardiac monitoring system of claim 15, wherein the processor and memory are disposed in the adherent device.

17. A method of collecting physiological data, the method comprising:
obtaining digital data representing an electrocardiogram of a patient;
detecting from the digital data a first episode of one of the plurality of cardiac rhythm types in the patient;
storing in an electronic memory a data snapshot of the first episode;
detecting from the digital data a second episode of one of the plurality of cardiac rhythm types in the patient; and
making one or more of the following determinations:
whether a respective refractory period has elapsed since the most recent recording of a data snapshot of an episode of the same rhythm type as the second episode, wherein the refractory period begins at an offset of the first episode and must elapse before an onset of the second episode;
whether storing a data snapshot of the second episode would exceed a respective maximum recording rate assigned to the rhythm type of the second episode; and
whether recording of a data snapshot of the second episode is inhibited by the recording of a different data snapshot; and
evaluating whether storing of a data snapshot of the second episode is prohibited by the outcome of any one of the one or more determinations made; and
storing in the electronic memory a data snapshot of the second episode only if such storing is not prohibited by the outcome of any of the one or more determinations made.

18. The method of claim 17, further comprising storing in the electronic memory an indication of the occurrence of each episode, regardless of whether a data snapshot of the episode is stored.

19. The method of claim 17, further comprising:
sensing a non-electrocardiogram physiological parameter of the patient; and
adjusting at least one criterion for storage of electrocardiogram data snapshots based at least in part on the sensed non-electrocardiogram physiological parameter of the patient.

* * * * *